(12) United States Patent
Welke

(10) Patent No.: US 9,675,924 B2
(45) Date of Patent: Jun. 13, 2017

(54) APPARATUS FOR THE RECOVERY OF HALOGENATED HYDROCARBONS

(71) Applicant: ZeoSys—Zeolithsystem—Forschungs- und Vertriebsunternehmen für Umweltschutz-, Medizin- und Energietechnik, GmbH., Berlin (DE)

(72) Inventor: Hartmut Welke, Ahrensfelde (DE)

(73) Assignee: ZEOSYS—ZEOLITHSYSTEME— FORSCHUNGS- UND VERTRIEBSUNTERNEHMEN FÜR UMWELTSCHUTZ-, MEDIZIN- UND ENERGIETECHNIK, GMBH (DE)

( * ) Notice: Subject to any disclaimer, the term of this patent is extended or adjusted under 35 U.S.C. 154(b) by 0 days.

(21) Appl. No.: 14/675,893

(22) Filed: Apr. 1, 2015

(65) Prior Publication Data

US 2015/0283494 A1 Oct. 8, 2015

(30) Foreign Application Priority Data

Apr. 3, 2014 (DE) .................... 20 2014 101 587 U

(51) Int. Cl.
*B01D 53/02* (2006.01)
*B01D 53/04* (2006.01)
(Continued)

(52) U.S. Cl.
CPC ........... *B01D 53/04* (2013.01); *B01D 19/001* (2013.01); *B01J 20/18* (2013.01); *B01J 20/20* (2013.01); *B01J 20/3408* (2013.01); *B01J 20/3416* (2013.01); *B01J 20/3466* (2013.01); *A61M 16/009* (2013.01); *B01D 53/002* (2013.01);
(Continued)

(58) Field of Classification Search
CPC ............... A61M 16/009; B01D 19/001; B01D 2253/108; B01D 2257/2066; B01D 2259/4009; B01D 2259/4533; B01D 53/002; B01D 53/04; B01D 53/0415;
(Continued)

(56) References Cited

U.S. PATENT DOCUMENTS

| 2,759,797 A * | 8/1956 | McKinnis ................ C01C 3/04 95/112 |
| 6,405,539 B1 | 6/2002 | Stach et al. |
| 2009/0101010 A1 | 4/2009 | Fuesting et al. |

FOREIGN PATENT DOCUMENTS

| DE | 101 18 768 A1 | 10/2002 |
| EP | 2644572 A1 | 10/2013 |

(Continued)

*Primary Examiner* — Christopher P Jones
(74) *Attorney, Agent, or Firm* — Schmeiser, Olsen & Watts, LLP

(57) ABSTRACT

An apparatus for recovering halogenated hydrocarbons has a desorption vessel which accommodates a sorbent which comprises the halogenated hydrocarbons, a steam generator which is configured to produce steam from water supplied to the steam generator and to introduce the steam which is produced into the desorption vessel in a manner such that the halogenated hydrocarbons are desorbed from the sorbent and absorbed by the steam, a cooling device which is configured to cool the steam supplemented with halogenated hydrocarbons in a manner such that a condensate is formed, and a collecting vessel which receives the condensate is provided.

7 Claims, 2 Drawing Sheets

(51) Int. Cl.
- *B01J 20/18* (2006.01)
- *B01J 20/20* (2006.01)
- *B01J 20/34* (2006.01)
- *B01D 19/00* (2006.01)
- *A61M 16/00* (2006.01)
- *B01D 53/00* (2006.01)

(52) U.S. Cl.
CPC .... *B01D 53/0415* (2013.01); *B01D 2253/108* (2013.01); *B01D 2257/2066* (2013.01); *B01D 2259/4009* (2013.01); *B01D 2259/4533* (2013.01)

(58) Field of Classification Search
CPC ........ B01J 20/18; B01J 20/20; B01J 20/3408; B01J 20/3416; B01J 20/3466
See application file for complete search history.

(56) References Cited

FOREIGN PATENT DOCUMENTS

| | | | |
|---|---|---|---|
| WO | 2007093640 | A1 | 8/2007 |
| WO | 2013106657 | A1 | 7/2013 |

* cited by examiner

APPARATUS FOR THE RECOVERY OF HALOGENATED HYDROCARBONS

CROSS-REFERENCE TO RELATED APPLICATION

This application claims priority to DE 20 2014 101 587.6, having a filing date of Apr. 3, 2014, the disclosure of which is hereby incorporated by reference in its entirety.

FIELD OF TECHNOLOGY

The following relates to an apparatus for recovering halogenated hydrocarbons.

BACKGROUND

Various technologies are known in the art for recovering inhalational anaesthetics.

The document WO 99/22845 A2 concerns a method and an apparatus for recovering gases, in particular anaesthetic gases, from zeolites. An absorber is filled with zeolite. A chemical vacuum pump is connected to the absorber to produce a vacuum. Next, the absorber is heated by means of a heating element and in that manner, the anaesthetic gas is driven out of the zeolite.

The document WO 2007/093640 A1 discloses a filter cartridge for recovering hydrocarbons and a corresponding method. The filter cartridge contains zeolites to which anaesthetic gases bind. In order to recover the anaesthetic gas, steam is fed through the filter cartridge.

A similar method for recycling anaesthetic gases from a filter cartridge is described in the document DE 101 18 768 A1.

SUMMARY

An aspect relates to improved technologies for recovering halogenated hydrocarbons.

This aspect is accomplished by the apparatus as claimed. Further embodiments form the subject matter of the dependent claims.

In one aspect, an apparatus is provided for recovering halogenated hydrocarbons which has a desorption vessel which accommodates a sorbent which comprises the halogenated hydrocarbons, a steam generator which is configured to produce steam from water supplied to the steam generator and to introduce the steam which is produced into the desorption vessel in a manner such that the halogenated hydrocarbons are desorbed from the sorbent and absorbed by the steam, a cooling device which is configured to cool the steam supplemented with halogenated hydrocarbons in a manner such that a condensate is formed, and a collecting vessel which receives the condensate.

An apparatus is provided which allows efficient recovery of the halogenated hydrocarbons.

As an example, the halogenated hydrocarbons may be inhalation anaesthetics, in particular anaesthetic gases such as sevoflurane, enflurane, isoflurane, haloethane or desflurane.

The sorbent comprises an adsorbent onto which the halogenated hydrocarbons are adsorbed. The adsorbent may be microporous. The adsorbent may be a material from the zeolite family. Zeolites are crystalline aluminosilicates which occur naturally in many different crystalline forms, but can also be produced by synthesis. As an example, Si-rich zeolites may be used as the adsorbent, preferably with a Si:Al ratio of more than 180:1 (corresponds to a $SiO_2:Al_2O_3$ ratio of 360:1). Alternatively, activated carbon may be used as the adsorbent.

The desorption vessel may accommodate one or more vessels of adsorbent, for example two. The sorbent is then placed in the one or more vessels of adsorbent. The vessel or vessels of adsorbent may be provided with a filter material on the base and/or the cover. The filter may have a pore size of 40 μm.

The steam generator may have a plurality of heating elements which can be connected up as a function of the power requirements in order to regulate the steam pressure. The steam generator may be configured with a filling level control. The steam generator is switched off, for example, if an upper or lower threshold of the filling level control is reached.

The cooling device may comprise two components, a precooler and an intermediate cooler. The precooler and the intermediate cooler may be disposed one after the other. With the precooler, freshly supplied water is preheated for the steam generator. The intermediate cooler serves to cool down the steam supplemented with the hydrocarbon to a temperature selected such that a condensate is formed. Furthermore, an aftercooler may be provided. A filter may be disposed between the intermediate cooler and the aftercooler. The filter may have a pore size of 5 μm. A filter candle for the filter may consist of a plastic, for example polypropylene. A housing of the filter may be formed from stainless steel, for example stainless steel with the material number 1.4404. The aftercooler may be operated with water from the mains supply.

In the collecting vessel, the desorbed hydrocarbons (desorbed materials) sink to the bottom, since they are heavier than water. The collecting vessel may be configured with a filling level control. A further collecting vessel may be provided which may also comprise a filling level control. The further collecting vessel may be connected to the collecting vessel. The two collecting vessels may be connected together in an upper region, allowing separation of the water. The collecting vessel and/or the further collecting vessel may be provided with a valve to withdraw the desorbed materials.

Furthermore, the apparatus may comprise a softening device which is located upstream of the steam generator and which is configured to reduce the hardness of the supplied water. The hardness of the water describes the equivalent concentration of ions dissolved in the water, in particular alkaline-earth metal ions. Under some circumstances, their anionic partners are also taken into consideration. The hardness of the water is raised, for example, by calcium and magnesium ions as well as strontium and barium ions ("hardeners"). The dissolved hardeners may form insoluble compounds, in particular limescale and lime soaps. As an example, the apparatus may be connected to the public water supply. The hardness of the water from the mains water supply varies from region to region. To reduce the hardness of the water, methods which are known per se may be employed, for example decarbonization and/or softening by ion exchange.

The softening device may have a prefilter located upstream thereof to filter the water. The prefilter may have a pore size of 100 μm. A polymer may be employed as the filter material of the prefilter, for example polypropylene.

In one embodiment, the apparatus may have a purification device which is located upstream of the steam generator and which is configured so as to remove at least a portion of the dissolved substances from the water of the supplied water.

The purification device may be configured so as to remove the dissolved substances by means of reverse osmosis. Reverse osmosis is a method for concentrating substances dissolved in liquids, in which the natural osmosis process is reversed using pressure. The water which is supplied, which contains a concentration of a substance which is to be reduced, is separated from a medium (for example water) in which the concentration is to be increased by a semipermeable membrane. The medium is placed under a pressure which is higher than the pressure which arises through the osmotic pressure to equilibrate the concentration. In this manner, the molecules of the substance move against their "natural" osmotic diffusion direction. They are forced out of the water into the medium.

The purification device may be located downstream of the softening device. A fine filter may be disposed between the softening device and the purification device to filter the water. The fine filter may have a pore size of 5 μm. The fine filter may be formed from a plastic, for example polypropylene.

A water tank may be provided to receive the softened and/or purified water.

By means of a combination of the softening device and the purification device (if necessary incorporating the prefilter and/or the fine filter), complete demineralization of the water may be obtained. Complete demineralization not only removes the hardeners from the water, but all ions. Complete demineralization may be obtained by means of a combination of cation and anion exchangers. The completely demineralized water may be supplied to the steam generator which then produces ultra-pure steam.

In a further embodiment, the apparatus may comprise a drying device which is located downstream of the steam generator and is configured so as to dry the steam before it is introduced into the desorption vessel. Moisture is at least partially removed from the steam. The moisture which is removed may be fed back to the steam generator. The drying device may be integrated into the steam generator.

In a further embodiment, the apparatus may comprise a buffer vessel which receives the halogenated hydrocarbons separated from the condensate. The buffer vessel may be connected to the collecting vessel and/or the further collecting vessel. The buffer vessel may be constructed with a filling level control.

Furthermore, the apparatus may comprise a compressed air device which is configured to convey the separated halogenated hydrocarbons from the buffer vessel into a transport vessel. The compressed air device may be operated with medically pure air.

The apparatus may be constructed as a sealed system.

The features disclosed for the apparatus are also relevant to a method for operating a unit of this type.

BRIEF DESCRIPTION

Some of the embodiments will be described in detail, with reference to the following figures, wherein like designations denote like members, wherein.

DETAILED DESCRIPTION

Figure 1:
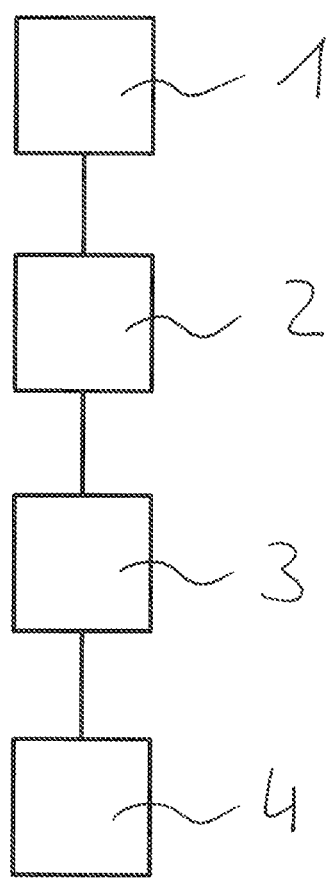
FIG. 1 is a diagrammatic representation of an apparatus.

The same reference numerals will be used below for identical components.

FIG. 1 shows a diagrammatic representation of an apparatus for recovering anaesthetic gases. A sorbent which comprises a zeolite with adsorbed anaesthetic gas (for example sevoflurane) is placed into a desorption vessel 1. Steam is produced by means of a steam generator 2 and introduced into the desorption vessel. The steam releases the anaesthetic gas from the zeolite and entrains it. The steam supplemented with anaesthetic gas is introduced into a condenser 3. In the condenser 3, the steam is cooled in a manner such that a condensate is formed which collects in the collecting vessel 4. In the condensate, the anaesthetic gas settles to the bottom of the collecting vessel 4 because it is heavier than water. The water is siphoned from the collecting vessel 4 so that the condensed anaesthetic gas (desorbed materials) can be collected and used again.

Figure 2:
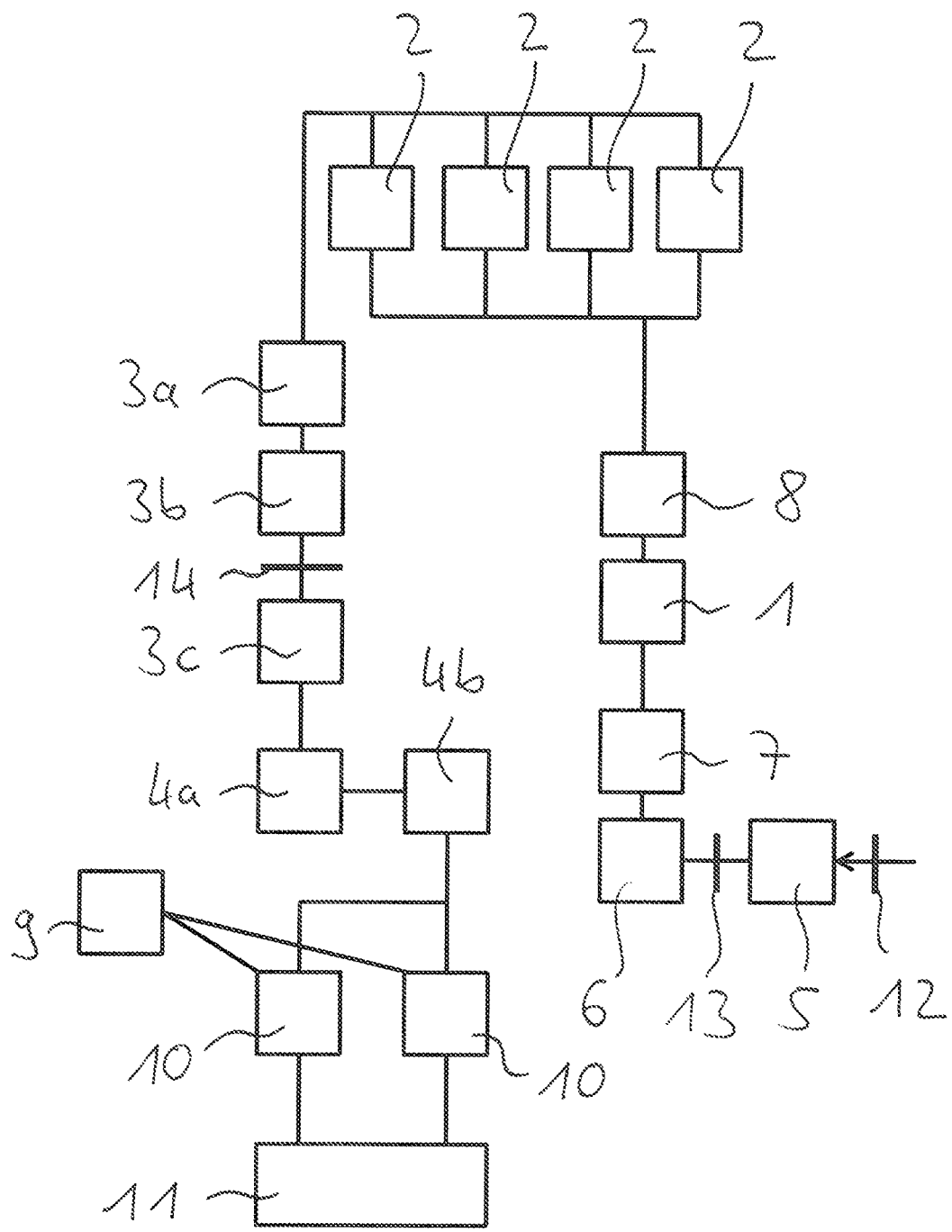
FIG. 2 is a diagrammatic representation of a further apparatus.

FIG. 2 shows a further embodiment of the apparatus. The apparatus comprises the following components: a CD (complete demineralization) zone with a softening unit 5, a reverse osmosis module 6 and a CD water vessel 7, a pure steam zone with an ultra-pure steam generator 1 and a dryer 8, a condensate zone with four desorption vessels 2, two stainless steel filters (not shown), a precooler 3a, an intermediate cooler 3b and a aftercooler 3c, a fine filter 14, two condensate collecting vessels 4 and two buffer vessels 10 as well as a compressed air zone with a compressed air unit 9.

The CD zone comprises the softening unit 5, the reverse osmosis module 6 as well as the CD water vessel 7. The softening unit 5, which constitutes the first stage of the CD water generation, is connected to a public water supply (municipal water). The second stage in the generation of CD water is constituted by the reverse osmosis. Filters 12, 13 are installed between the municipal water connection and the softening unit 5 as well as between the softening unit 5 and the osmosis module 6. The prefilter 12 has a pore size of 100 μm and the filter material used is a plastic, for example polypropylene. The fine filter 13 has a pore size of 5 μm and polypropylene is used as the filter material.

The steam generator 1 comprises eight electrical heating elements each with a power of 5 kW for the production of ultra-pure steam. The heating elements are connected as a function of the power requirement in order to adjust the pressure of the steam. The steam generator 1 is provided with a filling level control which has an upper and a lower threshold. When the level reaches the upper or the lower threshold, the steam generator 1 is switched off. In order to supply only dry steam to the desorption vessels 2, a dryer 8 is connected to the steam generator 1. The dryer 8 separates the moist components from the dry steam and ensures that they are returned to the water supply for the steam generator 1.

The apparatus is provided with four identical parallel desorption vessels 2 which are each provided with two vessels of adsorbent (not shown). The vessels of adsorbent have a volume of approximately 20 L and an internal diameter of 400 mm. The overall height of the desorption vessel 2 is 812 mm. The desorption vessel 2 can be opened manually in order to remove the vessels of adsorbent. The vessels of adsorbent can be opened for filling. To this end, a handle which is screwed to a threaded rod is manually unscrewed so that the cover can be removed. Both the cover and the base of each vessel of adsorbent are provided with a filter material which has a pore size of 40 μm.

The stainless steel filters with a pore size of 5 μm are disposed in parallel and can be operated individually or in parallel. To this end, the appropriate valves on the respective filters are opened. Above and below the filter is a valve. In addition, each filter has a CD water inlet and a waste water outlet. To operate a filter, the two filters, upper and lower, are opened. Furthermore, the filter may be rinsed with CD water from the CD water vessel. To rinse a filter, the valves on the filter have to be closed. To this end, the appropriate valves on the CD water inlet as well as on the outlet are opened. The CD water from the rinsing process is fed to the waste water line. The substance used for the filter candle and for the filter housing is stainless steel.

The precooler 3a is supplied with CD water in order to pre-heat freshly supplied CD water for the steam generator 1. Behind the precooler is an intermediate cooler 3b which is supplied with municipal water. An additional filter 14 with a pore size of 5 μm is disposed between the intermediate cooler 3b and the aftercooler 3c. The filter candle of the filter 14 consists of polypropylene and the filter housing is formed from stainless steel (material number 1.4404). The aftercooler 3c is also operated using municipal water as the cooling medium.

The collecting vessel 4a is connected to the aftercooler 3c and is connected at the bottom to a further collecting vessel 4b which contains a filling level control. The condensate collects in the collecting vessel 4a. In this regard, desorbed material sinks downwards because it is heavier than water. The desorbed material is also collected in the other collecting vessel 4b separately from the lighter water, and when the appropriate depth is reached, it is optionally fed from it to one of the buffer vessels 10. The supplemental collecting vessel 4b is also connected to the collecting vessel 4a in the upper region in order to separate the water again. It is also possible to remove the desorbed medium separately (for example for sampling) via a valve.

The buffer vessels 10 are connected to the collecting vessel 4a and the further collecting vessels 4b. Different desorbates may be stored in the buffer vessels 10. The buffer vessels 10 have a predetermined fill volume of 150 L. Both buffer vessels 10 are provided with a filling level control which is set to the filling level or the envisaged filled volume. The gross volume of each vessel is 220 L.

A compressed air supply is in the black room; it acts to convey the desorbed material by means of compressed air into an adjacent chamber (clean room) via pipework into a transport vessel 11. Medically pure air is used in this case; it is prepared with an adsorbing dryer as well as a pre-filter and an after-filter. Compressed air supply lines are connected to both buffer vessels 10 in order to produce the required pressure. Furthermore, both vessels 10 are connected with the transport line to the adjacent clean room in order to feed the desorbed materials from one of the buffer vessels 10 into the transport vessel 11. Both vessels 10 are connected to a sterile filter. This prevents contamination from the ambient air from gaining ingress into the medium in the buffer vessels 10.

The apparatus has the following technical specification:
softening output: max. 1000 liter/h
CD water output: 40 liter/h
ultra-pure steam output: 60 kg/h at 1.0 bar (overpressure)
electrical heating power: 40 kW
feed water consumption: max 65 liter/h.

The following materials are used:
parts coming into contact with product: stainless steel (material number 1.4404 or higher)
otherwise, stainless steel (material number 1.4301)
frame, stainless steel—square profile
outer casing of insulation, stainless steel (material number 1.4301).

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. An apparatus for recovering halogenated hydrocarbons comprising:
a desorption vessel which accommodates a sorbent which comprises the halogenated hydrocarbons;
a steam generator which is configured to produce steam from water supplied to the steam generator and to introduce the steam which is produced into the desorption vessel in a manner such that the halogenated hydrocarbons are desorbed from the sorbent and absorbed by the steam;
a cooling device which is configured to cool the steam supplemented with halogenated hydrocarbons in a manner such that a condensate is formed, the cooling device including a precooler configured to preheat water supplied to the steam generator, and an intermediate cooler configured to cool down the steam supplemented with the hydrocarbon to a temperature selected such that the condensate is formed; and
a collecting vessel which receives the condensate.

2. The apparatus as claimed in claim 1, further comprising a softening device which is located upstream of the steam generator and which is configured to reduce the hardness of the supplied water.

3. The apparatus as claimed in claim 1, further comprising a purification device which is located upstream of the steam generator and which is configured so as to remove at least a portion of dissolved substances from the water of the supplied water.

4. The apparatus as claimed in claim 1, further comprising a drying device which is located downstream of the steam generator and is configured so as to dry the steam before it is introduced into the desorption vessel.

5. The apparatus as claimed in claim 1, further comprising a buffer vessel which receives the halogenated hydrocarbons separated from the condensate.

6. The apparatus as claimed in claim 5, further comprising a compressed air device which is configured to convey the separated halogenated hydrocarbons from the buffer vessel into a transport vessel.

7. The apparatus as claimed in claim 1, wherein the apparatus is a sealed system.

\* \* \* \* \*

UNITED STATES PATENT AND TRADEMARK OFFICE
CERTIFICATE OF CORRECTION

Page 1 of 1

PATENT NO. : 9,675,924 B2
APPLICATION NO. : 14/675893
DATED : June 13, 2017
INVENTOR(S) : Hartmut Welke It is certified that error appears in the above-identified patent and that said Letters Patent is hereby corrected as shown below:

On the Title Page

Item (30)/Foreign Application Priority Data, please change "20 2014 101 587 U" to -- 20 2014 101 587.6 --

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*